United States Patent [19]

Howley et al.

[11] 4,419,446

[45] Dec. 6, 1983

[54] RECOMBINANT DNA PROCESS UTILIZING A PAPILLOMA VIRUS DNA AS A VECTOR

[75] Inventors: Peter M. Howley; Nava Sarver, both of Bethesda; Ming-Fan Law, Germantown, all of Md.

[73] Assignee: The United States of America as represented by the Department of Health and Human Services, Washington, D.C.

[21] Appl. No.: 221,565

[22] Filed: Dec. 31, 1980

[51] Int. Cl.³ .................... C12P 21/00; C12P 19/34; C12N 15/00; C12N 1/00

[52] U.S. Cl. .................................. 435/68; 435/172; 435/91; 435/317

[58] Field of Search .................. 435/172, 317, 68, 91

[56] References Cited

U.S. PATENT DOCUMENTS 4,237,224  12/1980  Cohen et al. ..................... 435/68

OTHER PUBLICATIONS

Science vol. 203, pp. 883–892 (Mar. 2, 1979).
Gissman et al., Proc. Natl. Acad. Sci. U.S.A., vol. 73, No. 4, pp. 1310–1313 Apr. 1976.
Rigby, Biochem. Soc. Symp. 44, pp. 89–102 (1979).
Mulligan et al., Nature, 277:108, 1979.
Gruss et al., Proc. Nat. Acad. Sci., Jan. 1981.
Wetzel, American Scientist, 1980, pp. 664–675.
Mulligan et al., Science, 209:1422–1427, 1980.
Pellicer et al., Science, 209:1414–1422, 1980.
Cohen et al., Proc. Natl. Acad. of Sci., 70:3240–3244, 1973.

*Primary Examiner*—Alvin E. Tanenholtz
*Attorney, Agent, or Firm*—John S. Roberts, Jr.

[57] ABSTRACT

A novel method and composition are provided for the replication and expression of exogenous genes in eukaryotic cells. A segment of a papilloma virus genome capable of extrachromosomal replication is linked to the foreign gene(s) using recombinant DNA techniques to provide a biologically functional replicon with a desired phenotypical property. The replicon is inserted into a eukaryotic cell by transformation, and the isolation of transformant provides cells for replication and expression of the DNA molecules present in the modified plasmid. The transforming region of the bovine papilloma virus provides a unique vector in that it provides both the capability of autonomous extrachromosomal replication but also the malignant transformed phenotype. Thus, genes which of themselves provide no selectable phenotypical property can be conveniently and efficiently introduced into eukaryotic cells and the transformants selected. The method is useful in that the foreign DNA is faithfully expressed and the gene products (proteins), such as pro-insulin (an insulin precursor) is synthesized.

6 Claims, No Drawings

RECOMBINANT DNA PROCESS UTILIZING A PAPILLOMA VIRUS DNA AS A VECTOR

PRIOR ART STATEMENT

Other vector systems for introducing genes into prokaryotic or eukaryotic cells are:

Mulligan, R. C., B. H. Howard, and P. Berg, *Nature*, 277:108, 1979.

Gruss, P. and G. Khoury, *Proc. Nat. Acad. Sci.*, January, 1981 (in press).

Wetzel, R., *American Scientist*, 1980, pages 664-675.

Mulligan, R. C., and P. Berg, *Science*, 209:1422-1427, 1980.

Pellicer, A., et al., *Science*, 209:1414-1422, 1980.

Cohen, S., et al, *Proc. Natl. Acad. of Sci.*, 70:3240-3244, 1973.

U.S. Pat. No. 4,237,224 to Cohen and Boyer utilizes plasmid vectors for introducing foreign DNA into unicellular organism; i.e., bacteria.

BACKGROUND OF THE INVENTION

Several methods are currently in use for delivering defined foreign DNA segments into eukaryotic cells. These include physical injection of DNA (Mueller et al., *Cell*, 15:579-585, 1978); fusion of DNA-containing liposomes (Ostro et al., *Nature*, 274:921-923, 1978; Dimitriadis, *Nature*, 274:923-924) or erythrocytes (Rechsteiner, *Natl. Cancer Inst. Monogr.*, 48:57-64, 1978) with target cells; and the direct application of naked DNA onto cells in the presence of calcium phosphate (Graham et al., *Virology*, 52:456-461, 1973) and marker DNA (Wigler et al., *Cell*, 11:223-232, 1977; Manel et al., *Nature*, 281:40-46, 1979; Wold et al., *Proc. Natl. Acad. Sci. USA*, 76:5684-5688, 1979).

More recently, insertion of DNA into recipient cells was achieved by using viral particles (SV40) in which a segment of the viral genome is covalently linked to defined nucleic acid segments (Mulligan et al., *Nature*, 277:108-114, 1979; Hammer et al., *Nature*, 281:35-40, 1979; Gruss and Khoury, *Proc. Natl. Acad. Sci. USA*, 1980 in press). While the SV40 vector system offers a rapid and efficient way to introduce foreign DNA's into permissive host cells, the system is limited by the size of DNA that can be accommodated within the virus particle. Moreover, since monkey cells are permissive for SV40 replication, infection by recombinant-SV40 particles culminates in cell death. SV40 DNA has not yet been exploited as a cloning vector in non-permissive rodent cells because (a) SV40 transformation is associated with integration of the viral genome, a process that may disrupt the integrity of the foreign DNA segment of interest; and (b) there is no indication that the gene will be active at detectable levels from the low integrated copy numbers which are sufficient for the expression of the SV40 transforming gene.

The present inventors have obtained good results utilizing certain papilloma virus genomes. Previously, studies on the molecular biology and genetics of the various papilloma viruses have been limited due to the lack of a cell-culture system suitable for propagating these viruses. However, studies on those papilloma viruses capable of inducing malignant transformation of eukaryotic cells in tissue culture indicate that the papillomavirus DNA is stably associated with the cell in an extrachromosomal state. Furthermore, evidence exists that the DNA of papilloma viruses not capable of inducing malignant transformation in eukaryotic cells remain stably associated with the cells (Lancaster and Meinke, *Nature*, 256:434-436, 1975).

Papers related to the biology of papilloma viruses and pipilloma virus DNA are listed below.

Lancaster, W. P., and W. Meinke, *Nature*, 256:434-436, 1975.

Lowry, D. R., et al, *Nature*, 287:72-74, 1980.

Howley, P. M., et al, *Viruses in Naturally Occurring Cancers*, Cold Spring Harbor Laboratory, pages 233-247, 1980.

Heilman, C. A., et al, *J. Virology*, 36:395-407, 1980.

The present invention provides unique vectors, segments of papilloma virus DNA for introducing foreign DNA into eukaryotic cells without the problems encountered in the prior art.

In the system described herein viral replication does not result in the death of the cell; many copies of the recombinant DNA are present per cell; by virtue of the transformed phenotype imparted by the bovine papilloma virus (BPV) DNA component no additional identification steps are required for identifying cells which have incorporated the foreign gene; the recombinant DNA exists exclusively as unintegrated extrachromosomal molecules; hence, the physical integration of the foreign gene is preserved and cells containing the foreign gene can be propagated indefinitely.

SUMMARY OF THE INVENTION

Methods and compositions are described for genetically transforming eukaryotic cells using segments of papilloma virus DNAs as vectors for introducing covalently joined genes or gene segments. Since papilloma viruses are persistent viruses, they each contain an intact replicon. Any subgenomic segment therefore containing an intact replicon is capable of replicating autonomously in susceptible eukaryotic cells. Known papilloma viruses include human papilloma viruses (types 1-8), bovine papilloma viruses (types 1-5), rabbit papilloma viruses, and papilloma viruses of sheep, deer, opposum, chimpanzee, chaffinch, dog and horse origina among others (Orth et al., Origina of Human Cancer, Cold Spring Harbor Conferences on Cell Proliferation 4:1043-1068, 1977). The bovine papilloma virus types 1 and 2, the sheep papilloma virus and deer papilloma virus are unique in that they are capable of transforming susceptible eukaryotic cells to a malignant phenotype of anchorable independence and absence of contact inhibition. This transformed phenotype can provide the basis of selection of those cells harboring the intact papilloma virus replicon and inserted foreign gene(s). Alternatively, linear segments of foreign genes with a selectable phenotypical trait can be ligated to the papilloma virus derived intact replicon and selected for following transformation of the eukaryotic cells. This can then serve as a vector for further selection of a foreign gene of interest but which does not encode a selectable phenotypical trait.

The present invention provides for a unique vector and the means for producing it. The vector is produced by cleaving a viral or circular plasmid DNA papilloma virus to provide a linear genome segment having an intact replicon and termini of a predetermined character. The vector is amplified in bacteria. Preferred papilloma virus are derived from BPV 1 DNA, BPV 2 DNA, BPV $1_{69T}$ DNA, sheep papilloma DNA and deer papilloma DNA.

The vector is combined with a foreign gene to produce a recombinant DNA. The linear segment of the vector is combined with a second linear DNA segment containing the foreign gene(s) or gene segment(s) which has termini ligatable to the termini of the vector. Either DNA segment has a phenotypical trait. The preferred papilloma virus DNA noted above have a malignant transforming phenotype such as anchorage independence of lack of contact inhibition, and this can be used to advantage in readily isolating transformants. Another phenotypical trait which either segment may have is resistance to growth inhibiting substance. Then growth is carried out in the presence of a sufficient amount of said growth inhibiting substance to inhibit the growth of non-transformed eukaryotic cell but is insufficient to inhibit the growth of transformants.

Producing the recombinant DNA utilizes techniques taught in U.S. Pat. No. 4,237,224, the teachings of which are incorporated herein by reference. The termini may be staggered and cohesive. The joining condition includes enzymatic ligation. The cohesive ends may be formed by staggered cleavage of the viral plasmid. The foreign gene DNA segment may be formed with a restriction enzyme. The cohesive termini may be formed by addition of nucleotides. The predetermined termini may be blunt end and the joining conditions include enzymatic ligation.

The recombinant DNA is introduced into eukaryotic cells where it functions episomally. Introduction into the cell is affected in the presence of calcium chloride, in the presence of DEAE dextran or by direct injection into the nucleus of the eukaryotic cells.

The transformants, recombinant DNA and cells are grown under transforming conditions. The transformants are isolated from the total population of eukaryotic cells by means of the phenotypical trait. Additionally, the gene product is isolated from the nutrient media or cell extract of the transformants.

Another aspect is that these first produced transformants may be used as a source for biologically functional DNA which are subsequently used to transform eukaryotic cells. Either method is a source of protein not normally produced by the eukaryotic cells.

The present invention provides for a unique vector for introducing foreign DNA into eukaryotic cells which has the following advantages.

First, the molecularly cloned BPV-1 DNA and a cloned 69% subgenomic fragment of the BPV-1 genome are very efficient in inducing transformed foci in susceptible mouse cells.

Second, the BPV DNA is present in the transformed cells in multiple copies (10–120) per cell exclusively as unintegrated episomal molecules, thus offering a natural means to amplify foreign DNA sequences covalently linked to the BPV transforming segment.

Third, since integration of the viral genome does not occur, the physical contiguity of the "passenger" DNA segment should be preserved.

Fourth, the transformed phenotype provides a marker for selecting those cells containing a foreign DNA segment covalently linked to the BPV transforming segment; thus, any cell line susceptible to BPV transformation is a potential recipient.

Fifth, BPV transformed cells grow faster than their non-transformed phenotype, facilitating the large scale production of cells containing the gene and possibly therefore the gene product.

The invention provides both a unique vector and a process for utilizing the vector to produce foreign gene products in eukaryotic cells.

Bovine papilloma virus type 1 (BPV-1) isolate 307 was purified from infected tissue and the supercoiled viral DNA isolated from the purified virions by differential salt precipitation (Hirt, J. Mol. Biol., 26:365–369, 1967) followed by isopycnic banding in CsCl-ethidium bromide gradients.

Purified viral DNA was characterized with respect to its sensitivity to several restriction endonucleases. A linear physical map of the 8 kilobase pair (kbp) closed circular BPV-1 DNA is shown in Table 1. Of the enconucleases tested, Bam HI, Hind III, Eco RI, Kpn and Hpa I were found to cleave the DNA at a single site. Three of these enzymes, Bam HI, Hind III and Eco RI also recognize a single restriction site in pBR322. This allows the cloning of the BPV-1 genome in pBR322 at three different sites. BPV-1 DNA was cloned at each of these sites, thereby generating three different recombinant molecules: BPV cloned at the Bam HI site of pBR322 (8-2); BPV cloned at the Hind III site of pBR322 (9-1) and BPV cloned at the Eco RI site of pBR322 (30-4).

Similarly BPV type 2 (isolate 319) was purified and its DNA characterized with respect to restriction endonuclease sensitivity. One enzyme, Hind III, recognizes a single site in BVP-2 DNA and also in pBR322 DNA. BPV-2 DNA was therefore cloned in pBR322 at the Hind III site.

Construction of a recombinant DNA containing the 69% transforming region of BPV-1 DNA: BPV-1 DNA cloned at the Bam HI site of pBR322 (8-2) was cleaved with Hind III and the 5.9 kb fragment containing the 69% transforming region of BPV (5.52 kb) and the small Bam HI/Hind III fragment of pBR322 (0.36 kb) was isolated on agarose gel. The fragment was then ligated to pBR322 at the Hind III site and the ligation mixture used to transform E. coli strain HB101. Ampicillin resistant tetracycline sensitive colonies were isolated and screened for the presence of a plasmid containing the 5.52 kb DNA fragment of BPV-1. One such colony was selected for subsequent study and its plasmid designated as 17-6.

Cleavage of 17.6 recombinant DNA with Bam HI/Hind III generated the 69% transforming region of BPV-1 henceforth designated as $BPV_{69T}$.

BPV-1 DNA linearized at the Bam HI site; BPV-1 DNA or BPV-2 DNA linearized at the Hind III site and $BPV_{69T}$ or BPV-1 DNA serve as vectors.

In order to employ the vector, the following steps are followed. The viral bovine papilloma genome covalently linked to pBR322 is separated from the plasmid by cleaving the recombinant DNA with either Bam HI or Hind III restriction endonuclease. Similarly, the foreign DNA is separated from the plasmid in which it was cloned. The $BPV_{69T}$ is covalently linked to the foreign DNA gene to form the desired recombinant DNA. The recombinant DNA is then linked to a plasmid and amplified in bacteria. Prior to transformation of eukaryotic cells, the recombinant DNA is separated from the plasmid by cleavage with restriction endonuclease.

Removed from its plasmid, the recombinant DNA can be introduced into eukaryotic cells.

The recombinant DNA is incubated with calcium chloride solution for 45 minutes at ambient temperature for forming a suspension. The suspension is applied to the eukaryotic cells and incubation continues for four hours at 37° C. The medium is then removed, the cells washed, and then treated with a solution containing 25% dimethyl sulfoxide for four minutes at ambient temperature. The cells are washed and fresh medium is applied. The maintenance medium is nutrient Delbecco modified Eagle's medium. The cells are incubated at 37° C. until transformed foci appear.

Individual foci are isolated and grown to a mass culture.

Convention techniques are used to characterize for foreign gene expression.

This process has the following outstanding features: After selection of transformed foci, no other selection means is necessary to identify cells which contain the foreign gene. That is, by virtue of the experimental procedure every transformed cell also contains the gene of interest.

The host DNA remains viable and cells containing the foreign gene can be propagated indefinitely. This is due to the fact that the interaction of the vector with the host cell results in transformation rather than in a lytic infection.

The recombinant DNA is not integrated into the host chromosomal DNA but exists and replicates as an episome. Hence, the physical integrity of the foreign gene is preserved, allowing for normal gene expression.

Viral episomal DNA exists in multiple copies per cell, averaging between 20 to 120 copies per diploid genome. This offers a natural means to amplify foreign genes which are covalently linked to BPV DNA.

VECTOR

Preparation of BPV DNA Genomes

Papilloma viruses are widely distributed in nature and typically induce benign skin tumor warts. These viruses are members of the papovirus group as are the polyomaviruses. Polyomaviruses such as SV40, polyoma and BK have been widely studied, but the lack of a suitable tissue culture system has hindered study on papillomaviruses.

In general, the proliferative skin changes induced by the papilloma viruses are limited to the epidermal cells and the viruses have a very narrow host range. However, some bovine papilloma viruses (BPV) are exceptional in that they induce fibropapillomas in their natural hosts (cows); these BPV can also induce cellular transformation in tissue culture and fibroblastic tumors in heterologous animals including hamsters, mice, and horses.

The bovine papilloma virus type 1, the bovine papilloma virus type 2, the deer papilloma virus, and the sheep papilloma virus are each capable of transforming mouse and hamster cells. Any papilloma virus DNA capable of transforming an eukaryotic cell to malignant transformed phenotype is acceptable. Papilloma viruses are derived from bovine, human, rabbit, sheep, deer, canine, equine, murine, or simian origin.

The above properties suggest that papilloma viruses in an appropriate form and able to sustain the desired characteristics described above could be used as a vector for introducing foreign DNA.

Molecularly cloned bovine papilloma virus DNA's were tested in the experiments described herein and efficacy as vectors established.

The following experiments have also established that a molecularly cloned fragment which contains 69% of the BPV-1 genome is a preferred vector. Subsequent studies show the utilization of $BPV_{69T}$ in a model system and applicability to other transformation operations in introducing foreign genes into eukaryotic cells.

A linear physical map of the 8-kilobase pair closed circular BPV-1 DNA genome from papilloma 307 is shown at the top of Table 1.

TABLE I

|  |  | Expt 1 | | Expt 2 | | Expt 3 |
| --- | --- | --- | --- | --- | --- | --- |
|  |  | C127 | NIH | C127 | NIH | C127 |
| BPV-1 DNA | Hind III — Bam HI — Eco RI — Hpa I — Hind III (0, .31, .60, .88, 1.0) | 112 | 298 |  |  | 244 |
| BPV-1 DNA linearized at 0.31 | Bam HI — Eco RI — Hpa I — Hind III — Bam HI | 114 | 278 | 106 | 207 | 316 |
| Segment $BPV_{69T}$ DNA | Bam HI — Hind III |  |  | 38 | 32 | 41 |
| Segment linearized at 0.31 and 0.88 | Bam HI — Hpa I |  |  | 0 | 0 |  |
| Segment linearized at .60 and .31 | Eco RI — Bam HI |  |  | 0 | 0 |  |
| Segment linearized at .88 and .31 | Hpa I — Bam HI |  |  | 0 | 0 |  |
| Segment linearized at .31 and .60 | Bam HI — Eco RI |  |  | 0 | 0 |  |
| Segment linearized at 1.00 and .31 | Hind III — Bam HI |  |  | 0 | 0 | 0 | scale: 0 1 2 3 4 5 6 7 8 kbp

Transformation of Mouse Cells by Intact and Subgenomic Fragments of BPV DNA

Mouse C127 cells were transfected with restriction endonuclease-digested DNA (0.1 to 0.5 μg per dish) using calf thymus DNA (25 μg ml$^{-1}$) as carrier (similar results were obtained when NIH3T3DNA was used as carrier). Foci were counted at 2 weeks for C127 cells and 4 or 5 days later for NIH3T3 cells. Results are expressed as focus forming units per ug of BPV DNA. pBR322 controls were included with each experiment and did not induce foci. A zero means that no foci were observed after testing 1 ug of DNA. In Experiment 2, the Bam HI DNA insert from clone 8-2 was digested with each of the other three enzymes. The DNA was electrophoresed in a 1% agarose gel after digestion with restriction endonuclease. The ethidium bromide-stained BPV DNA bands were cut out of the gel, electroeluted and transfected onto the cells as previously described. In Experiment 3, the 69% and 31% Bam HI/Hind III fragments used were clones 17-6 and 16-9, respectively. The DNAs were digested with Hind III/Bam HI, electrophoresed and transfected as in Experiment 2. kbp, Kilobase pairs.

Restriction endonucleases Hind III, Bam HI, Eco RI and Hpa I each cleave the viral DNA once, at 0, 0.31, 0.60 and 0.88 map units, respectively. The BPV DNA genome was cloned in pBR322 at the Bam HI site (clone 8-2) and also at the Hind III site (clone 9-1). After digestion with the enzyme used to insert BPV DNA into the pBR322 vector, the DNA was transfected into C127 and NIH 3T3 mouse cells. Within 2 weeks, foci of transformed cells appeared in each cell line (Table 1, Expt 1). These foci, which were more distinct on the C127 cells than in the NIH 3T3 cells, were indistinguishable morphologically from foci induced by BPV virions in the same cells. Transfection of NIH 3T3 cells resulted in two to three times more foci than observed in C127 cells with either the BPV-1 cloned DNAs (8-2 and 9-1). This greater sensitivity of the NIH 3T3 cells was also noted following infection with whole virions. In each cell line the two different BPV-1 DNA preparations induced a similar number of foci. BPV-2 DNA, which shows extensive sequence homology with BPV-1 DNA, was cloned in pBR322 at its unique Hind III site; after digestion with Hind III, this cloned DNA also induced foci in this transfection experiment.

Because BPV-1 DNA linearized at either the Hind III or Bam HI site was equally efficient in transforming these mouse cells, it seemed likely that some BPV-1 sequences might not be required for the induction of cellular transformation. Therefore, the ability of defined sub-genomic fragments of the cloned viral DNAs to transform the mouse cells was examined. The DNA fragments were prepared by digestion of the Bam HI BPV-1 DNA insert with a second restriction endonuclease which cleaved the BPV DNA at a unique site (Hind III, Eco RI and Hpa I). The BPV fragments were separated by agarose gel electrophoresis, individually eluted from the gel and transfected into the mouse cells. Of the various cleavage products tested, only the 69% Bam HI/Hind III fragment still induced foci, although its efficiency was lower than that of the complete BPV genome (Expt 2). The other sub-genomic fragments tested failed to induce foci.

To eliminate the possibility that the infectivity of the 69% Bam HI/Hind III fragment might be due to the transfection of additional BPV DNA sequences contaminating this DNA in the agarose gel, this fragment and the 31% Bam HI/Hind III fragment were each subcloned in pBR322 from the Bam HI BPV clone. Two subclones of each fragment were tested in the C127 mouse cell transfection assay. After separating the BPV DNA from the pBR DNA by digestion with Bam HI/Hind III, both the 69% fragment clones induced foci but the 31% fragment clones failed to do so (Expt 3). As noted previously, the specific infectivity of the 69% sub-genomic fragment was lower than that of the complete viral genome. Southern blot analysis of DNA from the transformed cells has indicated that, as expected, the transformants contained BPV DNA sequences from the 69% fragment and no sequences which hybridized with the 31% fragment.

The growth of the focus and the tumorigenicity of cells derived from it are documented in Table 2 (Lowy, et al, *Nature*, 287:72–74, 1980).

TABLE 2

Growth in Agar and Tumorigenicity of BPV DNA Transformants

| Transforming Agent | Colony Formation in Agar | Tumour Formation in Nude Mice |
|---|---|---|
| Control cells | 0 | 0/4 |
| BPV-1 virus | $1.4 \times 10^3$* | 4/4+ |
| Hind III genome, focus 52 | $0.6 \times 10^3$ | 4/4 |
| Bam HI, genome, focus 33 | $2.2 \times 10^3$ | 4/4 |
| Bam HI genome, focus 43 | $1.3 \times 10^3$ | 4/4 |
| 69% Fragment clone 17-6, focus 21 | $0.8 \times 10^3$ | 4/4 |
| 69% Fragment clone 17-6, focus 22 | $1.6 \times 10^3$ | 4/4 |
| 69% Fragment clone 17-2, focus 24 | $1.1 \times 10^3$ | 4/4 |
| 69% Fragment clone 17-2, focus 25 | $1.9 \times 10^3$ | 4/4 |

*No. of colonies per $10^4$ cells.
+No. of mice with tumours/no. of mice inoculated with cells.

Each BPV DNA transformant was isolated from a different dish of C127 cells to ensure that each was separately derived. Each focus of transformed cells was picked 3 weeks after transfection of DNA and propagated separately. Colony formation in 0.35% agar was carried out. Weanling nude mice were inoculated subcutaneously with $10^6$ transformed cells. Tumours were present in all animals by 3 weeks after inoculation. Control animals were observed for 8 weeks.

A good correlation has been noted between anchorage-independent growth of transformed cells and their capacity to be tumorigenic in nude mice. The ability of the BPV-transformed cells to form colonies in agar and to induce tumours in weaning nude mice has therefore been tested. Transformants derived from individual foci induced in C127 cells by the Hind III BPV genome, the Bam HI BPV genome and the 69% Bam HI/Hind III fragment all grew in soft agar; these cells also induced tumours in the mice after a latent period of 2–3 (weeks (Table 2). Mice inoculated with control cells did not develop tumours during 8 weeks of observation.

This subgenomic fragment is a desired vector. While its transforming efficiency is somewhat lower than the entire viral genome, it is sufficient to be useful. Moreover, the ability to use a smaller segment is highly desired for a vector because it may permit the stable cloning of larger foreign DNA segments in eukaryotic cells.

The vector can be linked by standard recombinant DNA techniques to the foreign gene of interest to produce a recombinant DNA capable of replication in eukaryotic cells.

The foreign DNA can be derived from a wide variety of sources. The DNA may be derived from eukaryotic or prokaryotic cells, viruses of bacteriophage. The genes introduced will be able to produce proteins which inclues hormones (such as growth hormones, gonadtropens, insulin, ACTH, etc.), serum proteins, enzymes, vitamins, and steroids as well as antibiotics and interferon. Additionally, virus proteins or portions of virus proteins may be produced which could be used as non-infectious vaccines. The model system described herein introduces the rat proinsulin gene with the protein (gene product) being proinsulin.

The foreign DNA fragments may have a molecular weight in the range of 0.5 to $20 \times 10^6$ and the DNA fragment may include one or more genes. Since the system does not result in the production of papilloma virus particles, the DNA is not encapsulated and theoretically no size constraint is therefore introduced.

A particular advantage of linking the foreign gene with the vector described above is the fact that by virtue of the transforming phenotype of the unique vector, the selection and isolation of cells that have incorporated the foreign genes is based simply on the isolation of transformed foci. Transformed foci are visualized with the naked eye and can be readily grown into mass culture.

Unlike prior art methods, a separate diagnostic medium is not required.

The recombinant DNA propagated in this manner could not have existed in nature. Thus, the invention provides recombinant DNA; i.e., vector plus foreign gene(s), which cannot naturally occur and which can be used for replication of foreign genes in eukaryotic cells. Most particularly, the genes introduced into the nucleus of the host eukaryotic cells do not integrate with the DNA of the host cell. The vector-foreign gene remains stably in the nucleus as an extrachromosomal circular DNA molecule.

Transformation

The vector-foreign gene is introduced into the host eukaryotic cells as naked DNA using the calcium phosphate-DNA coprecipitation method of Graham and Van der Eb (Virology 52: 456-461, 1973). By virtue of the ability of the BPV DNA to persist as a free plasmid in the transformed cells, the recombinant DNA does not integrate into the chromosomal DNA of the host cell. Hence, physical continuity of the foreign DNA is not interrupted. Moreover, no changes occur in the host chromosome. Typical host eukaryotic cells are of human, monkey, mouse, rat, rabbit, or hamster origin.

The vector-foreign gene recombinant DNA is stable and persists in transformed cells by replicating autonomously of the chromosome and then separating into daughter cells upon cell division. In known prior art systems in which the vector and gene are replicating autonomously, the host cell dies after several rounds of viral replication since the interaction of the virus with the host cell is lytic. Here, however, the interaction of the viral DNA and the host cell results in the transformation of cells rather than in cell death. Therefore, cell containing the recombinant DNA may be propagated indefinitely.

In addition, the recombinant DNA exists in many episomal copies (20 to 120) per diploid genome. This provides a natural means to amplify the foreign genes in endurdual cells and makes possible a good level of gene products.

Model System

The preferred vector, $BPV_{69T}$ DNA, was covalently linked to rat preproinsulin gene I ($rI_1$).

The experimental model consisted of the construction of a recombinant DNA molecule containing the 69% transforming region of BPV-1 DNA and the rat preproinsulin gene I ($rI_1$) which contains all the regulatory signals (the putative promoter, polyadenylation site and intervening sequence) necessary for faithful transcription.

Mouse cells transformed by the recombinant molecules were isolated and tested for the expression of the exogenous gene. Using several criteria, it was demonstrated that (i) multiple copies of preproinsulin DNA sequences are contained within transformed cells; (ii) these sequences exist predominantly if not exclusively, as free non-integrated plasmids in multiple copies per cell; (iii) the exogenous gene is transcribed into mRNA similar, if not identical, to authentic preproinsulin mRNA; (iv) these transcripts direct the synthesis of proinsulin protein; and (v) the gene product is secreted by the cells into the tissue culture medium in large amounts.

Materials and Methods

Cells and DNA Transformation. Mouse C127 I cells (Lowy et al, *J. Virol.*, 26:291-298, 1978) were maintained in Dulbecco's modified Eagle's medium (available from GIBCO, Long Island, N.Y.) supplemented with penicillin (10 U/ml), streptomycin (100 ug/ml) and 10% heat inactivated fetal bovine serum (available from M. A. Bioproducts, Walkersville, MD).

DNA transformation was performed using the calcium precipitation method (Graham et al, *Virology*, 52:456-461, 1973) followed by dimethyl sulfoxide (DMSO) enhancement (Stowe and Wilkie, *J. Gen. Virol.*, 33:447-458, 1976). Briefly, a 2X DNA-$CaCl_2$ solution (1 mM Tris pH 7.9/0.1 mM EDTA/250 mM $CaCl_2$/25 ug/ml calf thymus DNA/2.5 ug/ml recombinant DNA) was added to an equal volume of 2X HBS solution. (1X HBS=140 mM NaCl/25 mM HEPES/0.75 mM sodium phosphate pH 7.1) and the DNA precipitate allowed to form at room temperature over a 45 min. period. Portions representing 0.8 ug of the recombinant DNA were added to cell cultures in 60 mm Petri dishes containing 4 ml of fresh medium and incubation continued at 37° for 4 hrs. After changing medium, the cells were treated with 1 ml of 25% DMSO in HBS for 4 min. at room temperature. The monolayers were washed again and refed with fresh medium.

Analysis of Cellular DNA. Cellular DNA was extracted from confluent monolayers of transformed cells according to Gross-Bellard et al., *Eur. J. Biochem.*, 36:32-38, 1973, with slight modifications. The cell pellet was resuspended in proteinase lysine buffer (150 mM NaCl/25 mM EDTA/20 M Tris pH 8), proteinase K and SDS were added to final concentrations of 50 ug/ml and 1%, respectively, and the lysate incubated at 37° for 3 hr. The DNA was extracted with phenol, precipitated with ethanol, dissolved in 10 mM Tris pH 8, and dialyzed for 24 hr against the same buffer. The DNA solution was incubated with 50 ug/ml of RNAse A (Worthington) at 37° C. for 60 min. followed by treatment with Proteinase K, phenol extraction and dialysis as described above.

Blot Analysis. Restricted DNA was fractionated on 0.6% agarose gels. Partial depurination and denaturation of the DNA in situ was achieved by treating the gel, sequentially, with 0.25 N HCl (15 min, 2X); H$_2$O; 0.5 M NaOH/1 M NaCl (15 min, 2X); and 3 M NaCl/0.5 M Tris pH 7.4 (15 min, 2X) (Wahl et al, *Proc. Natl. Acad. Sci. USA*, 76:3683–3687, 1979). Denatured DNA's were transferred onto nitrocellulose filters (BA85, Schleicher and Schuell) according to a modification of the Southern blotting procedure (Southern, *J. Mol. Biol.*, 98:503–517, 1975; Ketner et al, *Proc. Natl. Acad. Sci. USA*, 73:1102–1106, 1976). Following transfer filters were dried in vacuo for 16 hr. at 60° C. and treated for 4 hr. at 65° in preincubation mixture (PM) containing 10X Denhardt buffer (0.2% each of ficol, BSA and polyvinyl pyrolidone) (Denhardt, *Biochem. Biophys. Res. Commun.*, 23:641–646, 1966), 3X SSC, and 50 ug/ml sheared denatured salmon sperm DNA. The filters were incubated for 20 hr. at 60° C. in PM containing 10% sodium dextran sulfate, 0.1% SDS and 5×10$^6$ CPM of denatured $^{32}$P-labeled DNA probe. After hybridization the filters were rinsed in 3X SSC, washed in 10X Denhardt solution (3 times at 60° C.) and then in 0.1X SSC/0.1% SDS (60° C.) until 10 ml of washing buffer registered <100 Cerenkov counts. Filters were dried and exposed to XR-2 x-ray film (Kodak) at −70° C.

Radiolabeled DNA's were prepared according to Rigby et al, *J. Mol. Biol.*, 113:237–251, 1977, in a reaction mixture containing 180 pmol each of α-$^{32}$P-dATP and α-$^{32}$P-dGTP (Amersham, 10 Ci/mmol), 180 pmol each of unlabeled dCTP and dTTP (Sigma), 1 mM DTT, 1 unit of *E. coli* DNA polymerase I (Boehringer) and 10$^{-9}$ g/ml of DNAse (Worthington).

Restriction endonucleases were obtained from New England Biolab and used in the recommended buffer system. Analytical and preparative reactions contained 1 u of enzyme per ug DNA. Incubation was for 60 min. at 37° C. after which the enzyme was inactivated (15 min. at 68° C.).

Preparative and analytical electrophoresis through horizontal gels was in Tris acetate buffer (5 mM Na acetate/1 mM EDTA/40 mM Tris pH 7.8) at either 2.5 V/cm for 16 hrs or 100 mA for 4 hours. Following electrophoresis the gels were stained with ethidium bromide (0.5 ug/ml) and the DNA visualized with short-wave UV light. DNA was recovered from the gel by electroelution into dialysis bag, extracted with phenol and precipitated with ethanol in the presence of 200 mM NaCl.

In situ hybridization. Cells were seeded in 60 mm plates. Twenty-four hours later the monolayers were transferred onto nitrocellulose filters, denatured and hybridized with $^{32}$P-labeled DNA probes essentially as described by Villarreal et al, *Science*, 196:183–186, 1977.

Construction of recombinant DNA's. The rat preproinsulin gene I DNA was the generous gift of A. Efstratiadis. The gene was originally isolated as a λ clone (Lomedico et al, *Cell*, 18:545–558, 1979, from rat chromosomal DNA library (Sargent et al, *Proc. Natl. Acad. Sci. USA*, 76:3256–3260, 1979. A 5.3 kb fragment was purified and cloned in pBR322 at the Bam HI site.

Construction of pBR322-insulin recombinant. A 1.62 kb segment containing the coding sequences of the gene, its intervening sequence and the regulatory signals at the 5' and 3' termini was generated from the cloned 5.3 kb DNA by a Bam HI/Hinc II digest. Following two purification steps through agarose gels, the DNA was electroeluted from the gel, extracted with phenol and precipitated with ethanol.

$^{32}$P-labeled synthetic Hind III linkers (Collaborative Research) were joined to the Hinc II site and the products digested with Hind III to generate tails with monomeric linkers. Modified 1.62 kb fragments were then ligated to the 4.0 kb fragment of Bam Hi/Hind III-cleaved pBR322 and the ligation mixture used to transform *E. coli* K12 strain HB101 (Hutchinson et al, *Gene*, 8:267–278, 1980).

Plasmid DNA from ampicillin-resistant tetracyclin-sensitive colonies was isolated (Wesnik et al, *Cell*, 3:315–325, 1974) following a chloramphenicol amplification step (Clewell, *J. Bact.*, 110:667–676, 1972) and analyzed with restriction enzymes for the presence of the 1.62 kb fragment. One such plasmid, prI$_1$ (1.62), was selected for further study.

Construction of a recombinant DNA containing the 69% transforming region of BPV-1 DNA. BPV-1 DNA cloned at the Bam HI site of pBR322 (8-2) was cleaved with Hind III and the 5.9 kb fragment containing the 69% transforming region of BPV (5.52 kb) and the small Bam HI/Hind III fragment of pBR322 (0.36 kb) was isolated on agarose gel. The fragment was then ligated to pBR322 at the Hind III site and the ligation mixture used to transform *E. coli* strain HB101. Ampicillin resistant tetracycline sensitive colonies were isolated and screened for the presence of a plasmid containing the 5.52 kb DNA fragment of BPV-1. One such colony was selected for subsequent study and its plasmid designated as 17-6. Cleavage of 17.6 recombinant DNA with Bam HI/Hind III generates the 69% transforming region of BPV-1 designated as BPV$_{69T}$.

Construction of pBR322-BPV insulin recombinant DNA. BPV$_{69T}$ was purified on agarose gel and ligated to the gel purified 1.62 kb fragment of prI$_1$. Following digestion with Hind III, the products were ligated to Hind III cleaved pBR322 and the resulting DNA used to transform *E. coli* strain HB101. DNA from ampicillin-resistant, tetracycline-sensitive colonies was isolated and analyzed with restriction endonucleases. One of the colonies containing the recombinant DNA (pBPV$_{69T}$-rI$_1$) was isolated amplified and used for subsequent studies.

Joining of Hind III linkers to DNA. Hind III linkers (0.05 O.D. units, Collaborative Research, Inc.) were heated for 2 minutes at 70[C and then cooled to room temperature. Phosphorylation of the 5' termini with [γ$^{32}$P] ATP (ICN) was done according to Maniatis et al, *Cell*, 15:687–701, 1978, in a 15 ul reaction volume. Phosphorylated linkers were then added to 500 ul of DNA (5 ug) in the same buffer. T$_4$ ligase (2 u, New England Biolab) was added and ligation allowed to proceed for 16 hours at 14° C. after which the enzyme was inactivated (15 min., 68° C.). Following a Hind III digest (to generate tails with monomeric linkers), the solution was extracted with phenol and concentrated by ethanol precipitation. Resulting DNA was then cloned in pBR322 as described.

Nuclease S1 mapping. Cytoplasmic RNA was prepared from approximately 10$^8$ cells as described by Khoury et al, supra, and the poly (A) containing fraction selected by chromatography on an oligo d(T) cellulose column (Aviv et al, *Proc. Natl. Acad. Sci. USA*, 69:1408–1412, 1972).

To obtain $^{32}$P labeled DNA probe, African Green Monkey kidney cells (AGMK) were coinfected with recombinant SV40 (SVL$_1$-rI$_1$) containing the preproinsulin gene (Gruss and Khoury, supra) and tsA28 as a helper and labeled 24 hr later with 0.1 mCi/ml of $^{32}$P orthophosphate (Amershal/Searle) in phosphate-free medium. After a 48-hour labeling period, viral DNA was prepared (Hirt, J. Mol. Biol., 26:365-369, 1967) and Form I DNA isolated on CsCl Et Br equilibrium gradient. The DNA was cleaved with Hae II/Bam HI, the 1560 base pair fragment purified on an agarose gel and used as a probe.

RNA transcripts were analyzed by the S1 nuclease method of Berk and Sharp, Cell, 12:721-732, 1977. Briefly, poly (A) containing RNA was mixed with $10^4$ CPM of $^{32}$P DNA probe (specific activity $10^6$ CPM/ug) the mixture precipitated with ethanol and the precipitate resuspended in 30 ul of formamide buffer (80% formamide/50 mM NaCl/50 mM PIPES pH 6.4). DNA duplexes were dissociated at 68° C. for 15 min., the mixture transferred to 50° C. water bath and hybridization continued for 3 hr at 50° C. The products were then treated with S1-nuclease (Miles) under the conditions described by Berk and Sharp, supra. Resulting DNA segments were precipitated buffer (30 mM NaOH/2 mM EDTA) and analyzed on a 1.4% alkaline agarose gel as described by McDonnell et al, J. Mol. Biol., 110:119-146, 1977, except that the gel was cast in 30 mM NaCl/0.2 mM EDTA and made alkaline by pre-running it in electrophoresis buffer for 60 min. Electrophoresis was at 40 V for 12 hr.

Protein analysis. Cells in 100 mm plates were washed 3 hr before labeling with Earle's balanced salt containing 5% normal medium and 2% dialyzed fetal bovine serum (GIBCO). They were labeled in the same medium with 200 uCi/ml of $^{35}$S L-cysteine (855.6 Ci/mmol, New England Nuclear) for 4 hr at 37° C. Medium was harvested, made 1% with respect to NP40 and 2 mM with respect to L-1-Tosylamide-2-phenyl-ethyl chloromethyl ketone (TPCK), clarified by centrifugation (SW 50.1, 35,000 RPM, 30 min) and the supernatant collected.

Cells were washed 3X with Tris-buffered saline (TBS), resuspended in 1 ml of lysis buffer [TBS containing 1% NP40/2 mM TPCK/1 mM DTT 2 mM phenyl methylsulfonylfluoride (PMSF)] and lysed for 20 min. on ice. The lysate was centrifuged as above and the supernatant collected. Samples equivalent to the medium from $10^6$ cells (1 ml) or extract from $1.5 \times 10^6$ cells (0.5 ml) were incubated with 100 ul of a 10% (v/v) suspension of protein A bearing *Staphylococcus aureus* (heat inactivated, formalin fixed Cowen I strain) (Kessler, J. Immunol., 115:1617-1624, 1975) for 2 hrs. at 4° C. after which nonspecifically adsorbed proteins were removed by centrifugation. The supernatant was mixed with 5 ul of anti-bovine insulin serum (Miles-Yeda, Israel) for 16 hr. at 4° C. For competitive binding studies 5 ul of the antiserum were preincubated with 2 ug of bovine insulin (Lilly) and preincubated for 30 min. at 4° C. after which the mixture was added to the samples and incubation continued for 16 hr. at 4° C.

*Staph A* (10 ul) was then added and incubation continued for 60 min. at 4° C. *Staph A* bound immune complexes were palleted, washed 3X with TBS containing 1% NP40 and eluted in electrophoresis sample buffer (62.5 mM Tris pH 6.3/2% SDS/5% β mercaptoethanol/10% glycerol/0.02% bromophenol blue). After heating at 95° C. for 3 min. the eluate was clarified by centrifugation.

Proteins were analyzed on a 1.5 mm$\times$120 mm SDS-polyacrylamide gels using the buffer system of Laemmli, Nature (London), 227:680-685, 1970. Gels consisted of a 10-17.5% polyacrylamide linear gradient or a linear 16% gel with a 3.75% stacker. Electrophoresis was at 20 mA for 4 hours. Following electrophoresis, gels were fixed for 60 min. in a solution containing 10% trichloroacetic acid/10% glacial acetic acid/30% methanol, impregnated with En$^3$Hance (New England Nuclear) for 60 min., and then treated with water for another 60 min. The gel was dried and exposed to XR-5 film (Kodak) at $-70°$ C.

Results

Construction of pBPV$_{69T}$-rI recombinant. The rat preproinsulin gene (rI$_1$) employed in this study was a generous gift of A. Efstratiadis, W. Gilbert and P. Lomedico. The gene was originally isolated as a λ clone (Lomedico et al, Cell, 18:545-558, 1979) from rat chromosomal DNA library (Sargent et al, Proc. Natl. Acad. Sci. USA, 76:3256-3260, 1979). A 5.3 kb fragment containing the rI$_1$ gene was cloned into pBR322 and a 1.62 kb segment containing the coding sequences, the intervening sequences and the regulatory signals of the rI$_1$ gene was then generated from the cloned 5.3 kb fragment by Bam HI/Hinc II digestion. Following modification of the Hinc II site to a Hind III site, the 1.62 kb segment was cloned into pBR322 and amplified in E. coli. Separation of this fragment from the plasmid was then accomplished by Bam HI/Hind III digestion followed by fractionation through an agarose gel.

A recombinant plasmid, pBPV$_{69T}$, consisting of the 69% transforming region of BPV-1 DNA (equivalent to 5.52 kb) has been described above. The 5.52 kb viral fragment was derived from the recombinant plasmid by Bam HI/Hind III digestion and purified by agarose gel electrophoresis. The purified 5.52 kb viral fragment (BPV$_{69T}$) was then ligated to the 1.62 kb insulin segment (rI$_1$) and the resulting products digested with Hind III. This step ensured that only one orientation of the recombinant molecule (ligated at the Bam HI site) is present in the mixture, thus allowing subsequent cloning at the Hind III site of pBR322.

Transformation of cells and screening of transformants for BPV and rI$_1$ sequences. BPV$_{69T}$-rI$_1$ DNA was separated from plasmid DNA by Hind III digestion and the resulting products used to transform mouse cells by the calcium phosphate technique and DMSO enhancement as described in Materials and Methods. Similarly, pBPV$_{69T}$, a recombinant plasmid containing only the 69% transforming region of BPV was cleaved with Bam HI/Hind III to generate the viral DNA sequences to be used as a control in transformation studies. Cells have then incubated at 37° C. and observed daily for formation of transformed foci.

Foci of transformed cells were first observed seven days after transfection and by day eleven were of sufficient size to be isolated. This was true for cells transformed either by BPV DNA alone or by the recombinant DNA. Moreover, the linearized recombinant DNA (PBV$_{69T}$-rI$_1$) transformed cells with high efficiency (approximately 200 transformed foci per ug DNA) indicating that linking the exogenous rat insulin DNA to BPV sequences does not interfere with its ability to transform. Transformed colonies were isolated and established as cell lines. It should be noted that BPV$_{69T}$-rI$_1$ transformed cells referred to in this study were each propagated from a single transformed focus rather than from singly-cloned cells.

At first it was essential to ascertain that BPV$_{69T}$-rI$_1$ transformed lines contained DNA sequences complementary to BPV DNA as well as to rI$_1$ DNA. For initial screening, the in situ hybridization method of Villarreal et al, *Science*, 196:183–186, 1977, was adopted in which specific DNA sequences contained within cells can be detected without prior isolation of the cellular DNA. Using this approach, it was found that each of the 48 individual clones isolated contained DNA sequences homologues to both the viral vector as well as to the rat preproinsulin gene. Several lines were selected arbitrarily for subsequent studies.

Analysis of DNA in transformed cell lines. The physical state of insulin gene in selected transformed cells was next analyzed by DNA blotting experiments. Using this analysis it was established (i) the gene exists as a free episome; (ii) the physical location of the insulin gene relative to the viral vector; and (iii) the copy number of the recombinant DNA molecule in transformed cells.

Total DNA isolated from transformed cells was treated with a restriction endonuclease that recognizes no site (Sst I) or a single site (Bam HI, EcoRI and Hind III) within $BPV_{69T}$-$rI_1$ DNA. Resulting products were fractionated on 0.6% agarose gels, transferred onto nitrocellular filters and hybridized with either $^{32}P$ labeled $BPV_{69T}$DNA or $rI_1$ DNA.

The results obtained for a representative $BPV_{69T}$-$rI_1$ transformed cell line (NS8) are described below. DNA treated with the no cut enzyme Sst-1 and hybridized to $^{32}P$ labeled BPV DNA gave rise to a prominent slow migrating DNA species. Digestion with the enzyme Bam HI (single cut for $BPV_{69T}$-$rI_1$) converted this species predominantly into linear Form III molecules. (Linearized $BPV_{69T}$-$rI_1$ DNA migrate faster than the linearized intact BPV DNA marker due to its smaller size—7.3 kb versus 8 kb.) Cleavage with Eco R1, another single cut enzyme for $BPV_{69T}$-$rI_1$ DNA, similarly converted this species predominantly into the 7.3 kb linear component. Recently it was established that BPV DNA exists in transformed mouse cells as a slow migrating complex of monomeric circular units as well as in monomeric supercoils. Both forms are converted to linearized Form III DNA upon cleavage by an endonuclease which recognizes a single site. Since the prominent slow migrating species observed in this study is similarly converted into Form III DNA after digestion with single site enzymes, it most likely also represents a non-integrated complex of monomeric units.

When the DNA was cleaved with Hind III (also a single site enzyme for $BPV_{69T}$-$rI_1$ DNA), again the great majority of the slow migrating band was converted to form III DNA. The results were somewhat different after Hind III cleavage in that a minor fraction of residual DNA still migrated as the slow migrating species. The residual slow migrating DNA represents recombinant DNA molecules that have upon circularization after transfection lost the Hind III site. The loss of the restriction site constituting the cohesive ends of transfecting DNA molecules has previously been described. The fact that not all molecules have lost the Hind III site clearly indicates DNA heterogeneity within this cell line. This may result either from the transfection of a single cell by multiple species of DNA or from the fact that this cell line was derived from a single transformed focus rather than from a single cell.

When $^{32}$-P labeled $rI_1$ DNA was used as a probe on duplicate blots (obtained from the same preparation or restricted DNA), it annealed to all fragments observed with the $^{32}P$ BPV probe. In addition, several DNA species were exposed which did not hybridize with $^{32}P$-BPV probe. Since these same bands were also demonstrated in DNA from untransformed C127 cells with the $^{32}P$-$rI_1$ DNA probe, it was concluded that they represent endogenous preproinsulin-related DNA sequences. DNA isolated from untransformed cells did not hybridize with any BPV-1 DNA sequences.

In addition to the predominant high molecular weight forms described above, several minor DNA species were also observed. Although it is possible that these bands represent integrated DNA forms, it is unlikely. First, previous studies of the present inventors have established that BPV DNA sequences persist in transformed mouse cells exclusively in a free, non-integrated episomal form. Second, if these minor bands represented integrated sequences, one would expect some variation between the hybridization pattern obtained using the $^{32}P$ BPV probe and that using the $^{32}P$ $rI_1$ probe (due to size heterogeneity in the flanking hose sequences). This is particularly apparent when assaying bolts of DNA cut with enzymes such as Bam HI and Hind III which separate the recombinant into its BPV and $rI_1$ components. As shown, the pattern obtained with four different endonucleases were identical (except for the additional endogenous insulin-like sequences seen with the $^{32}P$ $rI_1$ probe). Therefore, it was concluded that these minor species are episomal and result from either rearrangement of the recombinant DNA molecule or from the acquisition of cellular (or carrier) DNA sequences.

RNA Analysis. To ascertain whether insulin specific RNA transcripts are produced in $BPV_{69T}$-$rI_1$ transformed cells, the S1 nuclease mapping method of Berk and Sharp, *Cell*, 12:721–732, 1977, was adopted. In this analysis poly A containing RNA is hybridized to a $^{32}P$ labeled DNA probe under conditions which favor the formation of RNA-DNA duplexes. Hybrids thus formed are treated with S1 nuclease which hydrolyzes the single stranded DNA tails at the 3' and 5' termini of the duplex molecule as well as the unhydridized intervening sequences within the gene. The resulting products analyzed on alkaline agarose gels represent the exons present in specific mRNA's.

When authentic rat preproinsulin mRNA, derived from rat insulinoma cells (Chick et al, *Proc. Natl. Acad. Sci. USA*, 74:628–632, 1977) was hybridized with $^{32}P$ labeled $SVL_1$-$rI_1$ DNA probe, a single band of 402 nucleotides was detected. This band represents the coding sequences at the 3' end of the insulin gene. The 5' end of this fragment delineates the 3' terminus of the excised intervening sequences. The expected 42 nucleotide leader sequence is not resolved in the gel system used. RNA from $BPV_{69T}$-$rI_1$ transformed cell lines (NS6, NS8) similarly analyzed also protected a single 402 bases long DNA fragment. This band was seen in every $BPV_{69T}$-$rI_1$ transformed cell line tested. In contrast, control RNA from BPV transformed cells (1D14) did not protect this DNA fragment. Since the size of the DNA fragments obtained in these two cases is identical and since the 5' end is fixed by the splice junction, it was concluded that the entire coding region of the preproinsulin gene is represented in mRNA produced in $BPV_{69T}$-$rI_1$ transformed cells. It is also inferred from these observations that the polyadenylation signal at the 3' end of the gene is faithfully recognized.

For a comparison the pattern obtained using RNA from AGMK cells infected with SV40-insulin recombinant virus is included. In this case three predominant DNA fragments consisting of 402, 310 and 1420 nucleotides are detected. The 402 nucleotide fragment corresponds to the 3' exon of the authentic rat preproinsulin mRNA; the 310 fragment is derived from a transcript that uses an SV40 promoter and extends to the 5' end of the preproinsulin gene splice site; and the 1420 fragment is derived from a transcript which utilizes a polyadenylation site located within SV40 sequences.

The presence of only one insulin-specific transcript, corresponding to the coding sequences of the gene, in $BPV_{69T}$-$rI_1$ transformed cells suggests that viral termination signals are not involved in the transcription of rat preproinsulin gene. It should be noted, however, that DNA fragments less than 250 bases in length are not resolved in the gel system used. Hence, a definite statement concerning the 5' end of the transcript cannot be made at this time.

Protein Analysis. Having identified insulin specific RNA in $BPV_{69T}$-$rI_1$ transformed cells, the efficacy of the transcripts in directing translation and processing of polypeptides was investigated.

The production of insulin from its primary translational products involves several discrete steps. First, preproinsulin, a 110 amino acid in length, consisting of a hydrophobic preregion, plus the "B," "C" and "A" chains, is produced. The prehormone is then transferred through the microsomal membrane and the preregion peptide is cleaved off, thereby generating the proinsulin peptide. Subsequent folding of the proinsulin molecule brings the A and B chains into close proximity to allow the formation of disulfide bridges between the two chains. Once the disulfide bonds have been formed, the internal C chain is removed, thereby converting proinsulin to insulin.

Using a quantitative radioimmunoassay, tissue culture media from several cell lines were screened for the presence of a protein bearing insulin specific determinants. As shown in Table 3, media from $BPV_{69T}$-$rI_1$ transformed cells contained from 10 $\mu U/ml$ to more than 400 $\mu U/ml$ (1 U=48 ng) of material immunoreactive with anti-insulin serum. This represents a 2 to 80-fold increase over the 5 $\mu U/ml$ present in medium from untransformed C127 cells. When the medium of cells transformed by $BPV_{69T}$ alone was analyzed, only background levels (<6 $\mu U/ml$) were detected. This indicates that secretion of insulin or insulin-like material is not a property of BPV-transformed cells in general but rather a function of the exogenous DNA used in transformation.

The identity of the protein was established as that of rat proinsulin by the competitive immuno-precipitation studies followed by analysis on SDS-polyacrylamide gels. Cells were labeled with $^{35}S$-cysteine, an extract was prepared and immuno-precipitated with hamster anti-bovine insulin serum. Analysis of $BPV_{69T}$-$rI_1$ transformed cells [NS6(−), NS8(−), NS24(−)] demonstrated the presence of a prominent band identical in its electrophoretic mobility to proinsulin from $SVL_1$-$rI_1$ infected cells. This band was absent from the lysates prepared from cells transformed by BPV alone (ID14).

TABLE 3

| Mouse cell lines | Insulin secreted in 24 hrs by $10^6$ cells (uU/ml) | No. of lines/total | [%] |
|---|---|---|---|
| Transformed by $BPV_{69T}$-$rI_1$ | >400 | 24/48 | 50 |
| | 200–400 | 11/48 | 23 |
| | 40–200 | 10/48 | 21 |
| | 10–40 | 3/48 | 6 |

TABLE 3-continued

| Mouse cell lines | Insulin secreted in 24 hrs by $10^6$ cells (uU/ml) | No. of lines/total | [%] |
|---|---|---|---|
| Transformed by $BPV_{69T}$ | <5 | 6/6 | 100 |
| Untransformed C127 | <5 | 6/6 | 100 |

Rate of insulin production for a representative $BPV_{69T}$-$rI_1$ transformed cell line (NS8) = 400 uU/12 hrs/$10^6$ cells.

To confirm the identity of the band as proinsulin samples were incubated with antiserum previously neutralized with 2 $\mu g$ of bovine insulin. Under these conditions, no proinsulin-like protein was immunoprecipitated [NS6(+), NS8(+), NS24(+)].

To determine whether proinsulin was secreted into the medium, similar analyses on culture medium from $BPV_{69T}$-$rI_1$ transformed cells. A distinct band, the size of rat proinsulin was precipitated with anti-bovine sinulin serum [NS8(−)] but not with neutralized serum [NS8(+)]. Medium from cells transformed by BPV alone (1D14) did not contain this protein.

These results indicate that insulin specific RNA molecules produced in $BPV_{69T}$-$rI_1$ transformed cells are translated and that processing of these proteins results in the formation of proinsulin which is secreted into the medium.

Although the foregoing invention has been described in considerable detail by way of illustration and examples for purposes of clarity of understanding, it will be recognized that certain changes and modifications may be practiced within the scope of the appended claims.

We claim:

1. A process for producing a recombinant DNA suitable for introduction and replication in eukaryotic cells comprising the steps of:
   (a) cleaving bovine papilloma virus (BPV) type 1 or type 2 to produce a first linearized DNA segment selected from the group consisting of BPV-1 DNA cleaved at Bam HI; BPV-1 DNA cleaved at Hind III; BPV-2 DNA cleaved at Hind III; and the 69% subgenomic fragment; $BPV_{69T}$DNA, cleaved from BPV-1 DNA at Bam HI and Hind III,
   (b) combining said first linear DNA segment with a second linear DNA segment containing a foreign gene and having termini ligatable to the termini of the first segment under joining conditions to join said first and second segments to provide a functional recombinant DNA.

2. A process for persistent foreign gene replication in eukaryotic cells comprising the steps of:
   (a) cleaving bovine papilloma virus (BPV) type 1 or type 2 to produce a first linearized DNA segment selected from the group consisting of BPA-1 DNA cleaved at Bam HI; BPV-1 DNA cleaved at Hind III; BPV-2 DNA cleaved at Hind III and the 69% subgenomic fragment; $BPV_{69T}$DNA, cleaved from BPV-1 DNA at Bam HI and Hind III,
   (b) combining said first linear DNA segment and a second linear segment containing a foreign gene to form a recombinant DNA;
   (c) introducing the recombinant DNA into eukaryotic cells in the presence of calcium chloride to produce transformants of cells;
   (d) growing transformants under appropriate nutrient conditions until transformed foci appear;
   (e) amplifying individual foci to desired mass culture.

3. A Eukaryotic cloning vector consisting essentially of the subgenomic fragment BP $V_{69T}$ consisting of the 69 percent transforming region of bovine papilloma virus type 1 (BPV-1) cleaved from BPV-1 DNA at Bam HI and Hind III.

4. A recombinant DNA plasmid consisting essentially of the cloning vector of claim 3 and foreign DNA.

5. The recombinant DNA plasmid of claim 4 wherein the foreign DNA is eukaryotic or procoryotic.

6. A method of producing a protein foreign to an eukaryotic cell which comprises conducting the process of claim 2 until the foreign gene produces protein and then isolating the protein.

* * * * *